United States Patent
Abunassar

(10) Patent No.: US 11,998,449 B2
(45) Date of Patent: *Jun. 4, 2024

(54) REPAIR CLIP FOR VARIABLE TISSUE THICKNESS

(71) Applicant: EVALVE, INC., Santa Clara, CA (US)

(72) Inventor: Chad Abunassar, San Francisco, CA (US)

(73) Assignee: EVALVE, INC., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/933,667

(22) Filed: Sep. 20, 2022

(65) Prior Publication Data
US 2023/0011989 A1    Jan. 12, 2023

Related U.S. Application Data

(62) Division of application No. 17/067,382, filed on Oct. 9, 2020, now Pat. No. 11,464,636.
(Continued)

(51) Int. Cl.
    *A61F 2/24*    (2006.01)
(52) U.S. Cl.
    CPC ............ *A61F 2/246* (2013.01); *A61F 2/2466* (2013.01); *A61F 2220/0008* (2013.01); *A61F 2230/0093* (2013.01)
(58) Field of Classification Search
    CPC .................... A61F 2/246; A61F 2/2466; A61F 2220/0008; A61F 2230/0093;
(Continued)

(56) References Cited

U.S. PATENT DOCUMENTS

| 3,378,010 A | 4/1968 | Codling et al. |
| 3,874,388 A | 4/1975 | King et al. |

(Continued)

FOREIGN PATENT DOCUMENTS

| CA | 2 296 317 C | 1/2009 |
| EP | 0 558 031 B1 | 9/1993 |

(Continued)

OTHER PUBLICATIONS

Pham et al., "Material Properties of Aged Human Mitral Valve Leaflets," J Biomed Mater Res A. 102(8):2692-2703 (2014).
(Continued)

*Primary Examiner* — Brian A Dukert
*Assistant Examiner* — Rebecca Lynee Zimmerman
(74) *Attorney, Agent, or Firm* — SLEMAN & LUND LLP

(57) ABSTRACT

Fixation device for fixation of leaflets of a heart valve includes an elongate central member defining a longitudinal axis of the fixation device and first and second arms rotatable about at least one arm hinge point between an open position and a closed position. The fixation device further includes a first gripping element rotatable about a first gripping element axis of rotation to capture a first leaflet of a heart valve between the first gripping element and the first arm. The fixation device further includes a second gripping element rotatable about a second gripping element axis of rotation to capture a second leaflet of a heart valve between the second gripping element and the second arm. At least one of the first gripping element axis of rotation and the second gripping element axis of rotation is variably offset from the arm hinge point by an axis offset distance defined along the longitudinal axis.

20 Claims, 17 Drawing Sheets

Related U.S. Application Data

(60) Provisional application No. 62/914,211, filed on Oct. 11, 2019.

(58) Field of Classification Search
CPC ...... A61F 2250/0004; A61F 2250/0008; A61F 2250/0009; A61F 2250/0012
See application file for complete search history.

(56) References Cited

U.S. PATENT DOCUMENTS

| | | | |
|---|---|---|---|
| 4,007,743 A | 2/1977 | Blake | |
| 4,055,861 A | 11/1977 | Carpentier et al. | |
| 4,327,736 A | 5/1982 | Inoue | |
| 4,340,091 A | 7/1982 | Skelton et al. | |
| 4,657,024 A | 4/1987 | Coneys | |
| 4,693,248 A | 9/1987 | Failla | |
| 4,716,886 A | 1/1988 | Schulman et al. | |
| 4,795,458 A | 1/1989 | Regan | |
| 4,809,695 A | 3/1989 | Gwathmey et al. | |
| 4,930,674 A | 6/1990 | Barak | |
| 5,002,562 A | 3/1991 | Oberlander | |
| 5,069,679 A | 12/1991 | Taheri | |
| 5,098,440 A | 3/1992 | Hillstead | |
| 5,125,895 A | 6/1992 | Buchbinder et al. | |
| 5,147,370 A | 9/1992 | McNamara et al. | |
| 5,171,259 A | 12/1992 | Inoue | |
| 5,222,963 A | 6/1993 | Brinkerhoff et al. | |
| 5,271,544 A | 12/1993 | Fox et al. | |
| 5,327,905 A | 7/1994 | Avitall | |
| 5,330,501 A | 7/1994 | Tovey et al. | |
| 5,334,217 A | 8/1994 | Das | |
| 5,363,861 A | 11/1994 | Edwards et al. | |
| 5,389,077 A | 2/1995 | Melinyshyn et al. | |
| 5,403,326 A | 4/1995 | Harrison et al. | |
| 5,425,744 A | 6/1995 | Fagan et al. | |
| 5,450,860 A | 9/1995 | O'Connor | |
| 5,452,837 A | 9/1995 | Williamson, IV et al. | |
| 5,456,400 A | 10/1995 | Shichman et al. | |
| 5,456,674 A | 10/1995 | Bos et al. | |
| 5,478,353 A | 12/1995 | Yoon | |
| 5,542,949 A | 8/1996 | Yoon | |
| 5,562,678 A | 10/1996 | Booker | |
| 5,601,224 A | 2/1997 | Bishop et al. | |
| 5,601,574 A | 2/1997 | Stefanchik et al. | |
| 5,607,462 A | 3/1997 | Imran | |
| 5,607,471 A | 3/1997 | Seguin et al. | |
| 5,609,598 A | 3/1997 | Laufer et al. | |
| 5,611,794 A | 3/1997 | Sauer et al. | |
| 5,636,634 A | 6/1997 | Kordis et al. | |
| 5,695,504 A | 12/1997 | Gifford, III et al. | |
| 5,713,911 A | 2/1998 | Racenet et al. | |
| 5,716,417 A | 2/1998 | Girard et al. | |
| 5,741,297 A | 4/1998 | Simon | |
| 5,755,778 A | 5/1998 | Kleshinski | |
| 5,782,239 A | 7/1998 | Webster, Jr. | |
| 5,797,960 A | 8/1998 | Stevens et al. | |
| 5,810,847 A | 9/1998 | Laufer et al. | |
| 5,814,097 A | 9/1998 | Sterman et al. | |
| 5,843,178 A | 12/1998 | Vanney et al. | |
| 5,849,019 A | 12/1998 | Yoon | |
| 5,855,601 A | 1/1999 | Bessler et al. | |
| 5,976,159 A | 11/1999 | Bolduc et al. | |
| 6,015,417 A | 1/2000 | Reynolds, Jr. | |
| 6,048,351 A | 4/2000 | Gordon et al. | |
| 6,079,414 A | 6/2000 | Roth | |
| 6,117,144 A | 9/2000 | Nobles et al. | |
| 6,120,496 A | 9/2000 | Whayne et al. | |
| 6,149,658 A | 11/2000 | Gardiner et al. | |
| 6,165,183 A | 12/2000 | Kuehn et al. | |
| 6,182,664 B1 | 2/2001 | Cosgrove | |
| 6,193,734 B1 | 2/2001 | Bolduc et al. | |
| 6,200,315 B1 | 3/2001 | Gaiser et al. | |
| 6,217,528 B1 | 4/2001 | Koblish et al. | |
| 6,269,819 B1 | 8/2001 | Oz et al. | |
| 6,290,674 B1 | 9/2001 | Roue et al. | |
| 6,312,447 B1 | 11/2001 | Grimes | |
| 6,332,880 B1 | 12/2001 | Yang et al. | |
| 6,346,074 B1 | 2/2002 | Roth | |
| 6,419,696 B1 | 7/2002 | Ortiz et al. | |
| 6,461,366 B1 | 10/2002 | Seguin | |
| 6,482,224 B1 | 11/2002 | Michler et al. | |
| 6,496,420 B2 | 12/2002 | Manning | |
| 6,544,215 B1 | 4/2003 | Bencini et al. | |
| 6,551,303 B1 | 4/2003 | Van Tassel et al. | |
| 6,575,971 B2 | 6/2003 | Hauck et al. | |
| 6,599,311 B1 | 7/2003 | Biggs et al. | |
| 6,626,930 B1 | 9/2003 | Allen et al. | |
| 6,629,534 B1 | 10/2003 | St. Goar et al. | |
| 6,669,687 B1 | 12/2003 | Saadat | |
| 6,695,866 B1 | 2/2004 | Kuehn et al. | |
| 6,719,767 B1 | 4/2004 | Kimblad | |
| 6,752,813 B2 | 6/2004 | Goldfarb et al. | |
| 6,770,083 B2 | 8/2004 | Seguin | |
| 6,797,002 B2 | 9/2004 | Spence et al. | |
| 6,837,867 B2 | 1/2005 | Kortelling | |
| 6,855,137 B2 | 2/2005 | Bon | |
| 6,875,224 B2 | 4/2005 | Grimes | |
| 6,908,481 B2 | 6/2005 | Cribier | |
| 6,926,730 B1 | 8/2005 | Nguyen et al. | |
| 7,011,669 B2 | 3/2006 | Kimblad | |
| 7,101,395 B2 | 9/2006 | Tremulis et al. | |
| 7,112,207 B2 | 9/2006 | Allen et al. | |
| 7,125,421 B2 | 10/2006 | Tremulis et al. | |
| 7,226,467 B2 | 6/2007 | Lucatero et al. | |
| 7,556,632 B2 | 7/2009 | Zadno | |
| 7,563,267 B2 | 7/2009 | Goldfarb et al. | |
| 7,569,062 B1 | 8/2009 | Kuehn et al. | |
| 7,604,646 B2 | 10/2009 | Goldfarb et al. | |
| 7,635,329 B2 | 12/2009 | Goldfarb et al. | |
| 7,655,015 B2 | 2/2010 | Goldfarb et al. | |
| 7,666,204 B2 | 2/2010 | Thornton et al. | |
| 7,736,388 B2 | 6/2010 | Goldfarb et al. | |
| 7,811,296 B2 | 10/2010 | Goldfarb et al. | |
| 7,972,323 B1 | 7/2011 | Bencini et al. | |
| 7,981,139 B2 | 7/2011 | Martin et al. | |
| 8,057,493 B2 | 11/2011 | Goldfarb et al. | |
| 8,062,313 B2 | 11/2011 | Kimblad | |
| 8,118,822 B2 | 2/2012 | Schaller et al. | |
| 8,216,230 B2 | 7/2012 | Hauck et al. | |
| 8,216,256 B2 | 7/2012 | Raschdorf, Jr. et al. | |
| 8,303,608 B2 | 11/2012 | Goldfarb et al. | |
| 8,500,761 B2 | 8/2013 | Goldfarb et al. | |
| 8,734,505 B2 | 5/2014 | Goldfarb et al. | |
| 8,740,920 B2 | 6/2014 | Goldfarb et al. | |
| 9,510,829 B2 | 12/2016 | Goldfarb et al. | |
| 10,076,415 B1 | 9/2018 | Metchik et al. | |
| 10,105,222 B1 | 10/2018 | Metchik et al. | |
| 10,123,873 B1 | 11/2018 | Metchik et al. | |
| 10,130,475 B1 | 11/2018 | Metchik et al. | |
| 10,136,993 B1 | 11/2018 | Metchik et al. | |
| 10,159,570 B1 | 12/2018 | Metchik et al. | |
| 10,231,837 B1 | 3/2019 | Metchik et al. | |
| 10,238,493 B1 | 3/2019 | Metchik et al. | |
| 10,245,144 B1 | 4/2019 | Metchik et al. | |
| D847,983 S | 5/2019 | Ho et al. | |
| 10,314,586 B2 | 6/2019 | Greenberg et al. | |
| 10,413,408 B2 | 9/2019 | Krone et al. | |
| 10,507,109 B2 | 12/2019 | Metchik et al. | |
| 10,517,726 B2 | 12/2019 | Chau et al. | |
| 10,524,792 B2 | 1/2020 | Hernandez et al. | |
| 10,595,997 B2 | 3/2020 | Metchik et al. | |
| 10,646,342 B1 | 5/2020 | Marr et al. | |
| 10,779,837 B2 | 9/2020 | Lee et al. | |
| D902,403 S | 11/2020 | Marsot et al. | |
| 10,856,988 B2 | 12/2020 | McNiven et al. | |
| 2002/0013571 A1 | 1/2002 | Goldfarb et al. | |
| 2002/0183787 A1 | 12/2002 | Wahr et al. | |
| 2003/0069593 A1 | 4/2003 | Tremulis et al. | |
| 2003/0167071 A1 | 9/2003 | Martin et al. | |
| 2004/0034365 A1 | 2/2004 | Lentz et al. | |
| 2004/0044350 A1 | 3/2004 | Martin et al. | |
| 2005/0267493 A1 | 12/2005 | Schreck et al. | |
| 2006/0020275 A1 | 1/2006 | Goldfarb et al. | |
| 2007/0038293 A1 | 2/2007 | St. Goar et al. | |

(56) References Cited

U.S. PATENT DOCUMENTS

| | | |
|---|---|---|
| 2007/0197858 A1* | 8/2007 | Goldfarb .......... A61B 17/0401 600/37 |
| 2017/0042546 A1 | 2/2017 | Goldfarb et al. |
| 2017/0049455 A1 | 2/2017 | Seguin |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |
| 2018/0092661 A1 | 4/2018 | Prabhu |
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A2 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |

FOREIGN PATENT DOCUMENTS

| | | |
|---|---|---|
| EP | 1 383 448 B1 | 6/2008 |
| FR | 2 768 324 A1 | 3/1999 |
| FR | 2 768 325 B1 | 11/1999 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/057289 A1 | 4/2015 |
| WO | WO 2016/178722 A1 | 11/2016 |
| WO | WO 2018/093663 A1 | 5/2018 |

OTHER PUBLICATIONS

Saxena, "Echocardiographic Diagnosis of Chronic Rheumatic Valvular Lesions," Global Heart vol. 8, Issue 3, Sep. 2013, pp. 203-212.
Silver et al., "Morphology of the Human Tricuspid Valve," Circulation, vol. XLIII, Mar. 1971, pp. 333-348.

* cited by examiner

REPAIR CLIP FOR VARIABLE TISSUE THICKNESS

CROSS-REFERENCE TO RELATED APPLICATIONS

This application is a divisional application of U.S. patent application Ser. No. 17/067,382, filed Oct. 9, 2020, now allowed, which claims priority to U.S. Provisional Application Ser. No. 62/914,211 filed on Oct. 11, 2019, the contents of which are hereby incorporated by reference in their entirety.

FIELD OF DISCLOSED SUBJECT MATTER

The disclosed subject matter is directed to medical devices for the endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall can be damaged or otherwise dysfunctional. Commonly, the valve annulus can be damaged, dilated, or weakened limiting the ability of the mitral valve to close adequately against the high pressures of the left ventricle.

DESCRIPTION OF RELATED ART

Treatments for mitral valve regurgitation rely on valve replacement or repair including leaflet and annulus remodeling, the latter generally referred to as valve annuloplasty. Another technique for mitral valve repair, which relies on suturing adjacent segments of the opposed valve leaflets together is referred to as the "bow-tie" or "edge-to-edge" technique. Preferably, the use of devices and systems should not require open chest access and, rather, be capable of being performed either endovascularly, i.e., using devices, such as a catheter, which are advanced to the heart from a point in the patient's vasculature remote from the heart. Furthermore, such devices and systems should allow for repositioning and optional removal of a fixation device (i.e., valve repair clip) prior to fixation to ensure optimal placement. Such devices and systems likewise can be useful for repair of tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a fixation device for treating a patient.

In accordance with the disclosed subject matter, a fixation device for fixation of leaflets of a heart valve includes an elongate central member defining a longitudinal axis of the fixation device, and first and second arms rotatable about at least one arm hinge point between an open position and a closed position. The fixation device further includes a first gripping element rotatable about a first gripping element axis of rotation to capture a first leaflet of a heart valve between the first gripping element and the first arm. The fixation device further includes a second gripping element rotatable about a second gripping element axis of rotation to capture a second leaflet of a heart valve between the second gripping element and the second arm. At least one of the first gripping element axis of rotation and the second gripping element axis of rotation is variably offset from the arm hinge point by an axis offset distance defined along the longitudinal axis.

A variety of configuration can be provided in accordance with the disclosed subject matter. For example, the first gripping element and the second gripping element can be operatively coupled together whereby the first gripping element axis of rotation and the second gripping element axis of rotation define a single axis of rotation. Furthermore, the at least one of the first gripping element axis of rotation and the second gripping element axis of rotation can be located at an end of the respective gripper element proximate the elongate central member. Additionally, each of the first gripping element and the second gripping element can be operatively coupled to the elongate central member. The at least one of the first gripping element axis of rotation and the second gripping element axis of rotation can be biased toward the at least one arm hinge point for automatic adjustment of the axis offset distance upon capture of a native leaflet.

In accordance with another aspect, each of the first gripping element axis of rotation and the second gripping element axis of rotation can be variably offset from the arm hinge point. A first offset distance can be defined between the arm hinge point and the first gripping element axis of rotation, and a second offset distance can be defined between arm hinge point and the second gripping element axis of rotation, wherein the first offset distance is independent of the second offset distance.

Alternatively, the first gripping element axis of rotation can be parallel to and spaced along the longitudinal axis from the second gripping element axis of rotation. Furthermore, the axis offset distance between the at least one hinge point and the at least one of the first gripping element axis of rotation and the second gripping element axis of rotation can be incrementally selectable. Furthermore, the at least one of the first gripping element axis of rotation and the second gripping element axis of rotation can include at least one connector pin, and the elongate central member can include a plurality of pin holes defined therein configured to engage with the connector pin. The pin holes can be spaced longitudinally along the elongate central member.

Alternatively, at least one of the first gripping element axis of rotation and the second gripping element axis of rotation can be variably adjustable along a channel defined in the elongated central member, wherein the device can further include at least one shim disposed in the channel to limit maximum axis offset distance. Furthermore, the at least one of the first gripping element axis of rotation and the second gripping element axis of rotation can be biased away from the at least one arm hinge point, the device can further comprise at least one shim to limit maximum axis offset distance.

In accordance with another aspect, the at least one of the first gripping element axis of rotation and the second gripping element axis of rotation can be a flex portion defined along a length of the respective gripping element. The respective gripping element having the flex portion can be attached to the elongate central member. Alternatively, the respective gripping element having the flex portion can be attached to a corresponding one of the first and second arms.

Alternatively or additionally, the at least one of the first gripping element axis of rotation and the second gripping element axis of rotation can be a compliant hinge configured to variably change depending on a thickness of a captured native leaflet of the heart valve. The gripping element having the compliant hinge can be coupled to the elongate central member. Alternatively, the gripping element having the compliant hinge can be coupled to the corresponding arm.

Furthermore, at least one arm can include a trough having a trough bottom defining a trough reference plane, and wherein the arm hinge point can be offset from the trough reference plane by a trough offset distance defined along the longitudinal axis. The fixation device can be releasably coupled to the distal end of a delivery shaft.

DETAILED DESCRIPTION

Figure 1:
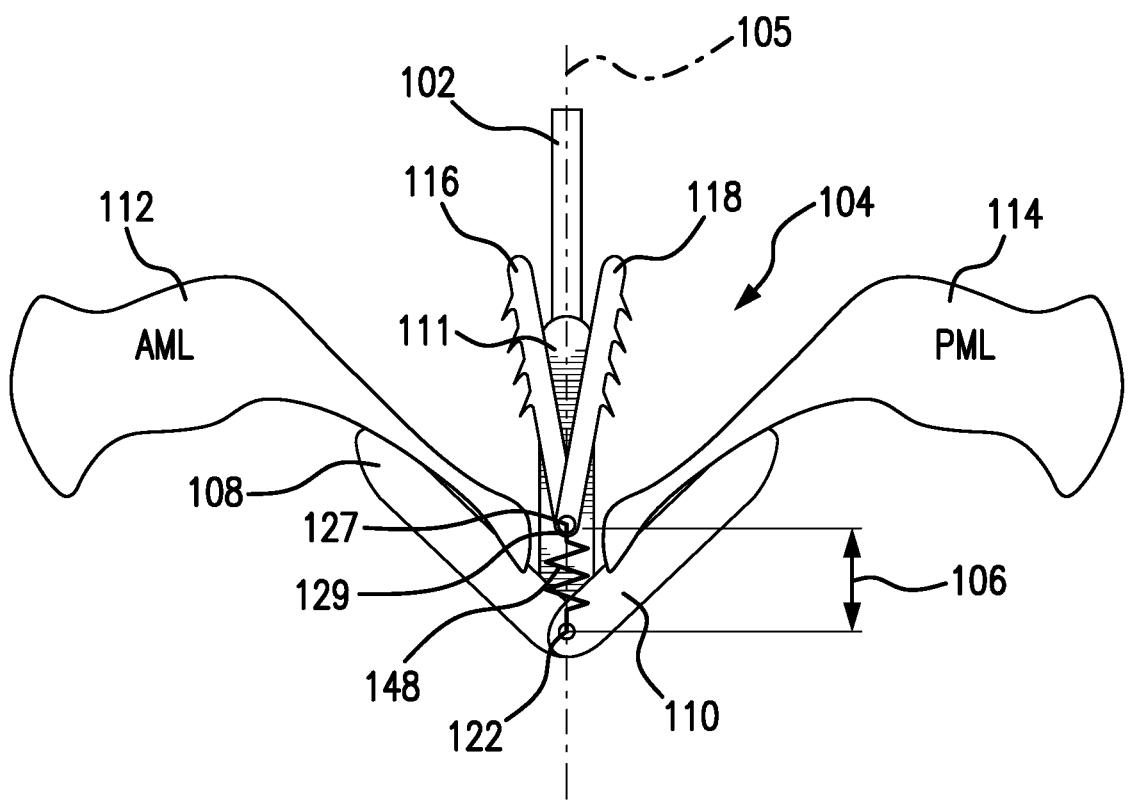
FIG. 1 is a front schematic view of an exemplary embodiment of a fixation device in accordance with the disclosed subject matter.

Reference will now be made in detail to the various exemplary embodiments of the disclosed subject matter, exemplary embodiments of which are illustrated in the accompanying drawings.

The fixation device for use with the disclosed subject matter provides an edge-to-edge transcatheter valve repair option for patients having various conditions, including regurgitant mitral valves or tricuspid valves. Transcatheter (e.g., trans-septal) edge-to-edge valve repair has been established using a fixation device, such as the MitraClip Transcatheter Mitral Valve Repair device. These fixation devices generally are configured to capture and secure opposing native leaflets using two types of leaflet contacting elements. The first element is a sub-valvular arm (also known as a distal element or fixation element) to contact the ventricular side of a native leaflet to be grasped. With the arm positioned underneath to stabilize the native leaflet in a beating heart, a second gripping element (e.g., a proximal element) can be lowered or moved into contact with the atrial side of the native leaflet to capture the leaflet therebetween. Once each opposing leaflet is captured by a respective arm and gripper element, the fixation device can be closed by raising or moving the arms toward a center of the fixation device such that the leaflets are brought into coaptation, which results in a reduction in valvular regurgitation during ventricular systole. Furthermore, a covering can be provided on the arms and/or gripper elements to facilitate tissue ingrowth with the captured leaflets.

Additional details of an exemplary fixation device in accordance with the disclosed subject matter are set forth below. Furthermore, a number of patents and publications disclose additional details and aspects of such fixation devices and related operations. See, for example, U.S. Pat. No. 7,226,467 to Lucatero et al.; U.S. Pat. No. 7,563,267 to Goldfarb et al.; U.S. Pat. No. 7,655,015 to Goldfarb et al.; U.S. Pat. No. 7,736,388 to Goldfarb et al.; U.S. Pat. No. 7,811,296 to Goldfarb et al.; U.S. Pat. No. 8,057,493 to Goldfarb et al.; U.S. Pat. No. 8,303,608 to Goldfarb et al.; U.S. Pat. No. 8,500,761 to Goldfarb et al.; U.S. Pat. No. 8,734,505 to Goldfarb et al.; U.S. Pat. No. 8,740,920 to Goldfarb et al.; U.S. Pat. No. 9,510,829 to Goldfarb et al.; U.S. Pat. No. 7,635,329 to Goldfarb et al.; U.S. Patent Application Publication No. 2017/0042546 to Goldfarb et al.; U.S. Patent Application Publication No. 2017/0239048 to Goldfarb et al.; U.S. Patent Application Publication No. 2018/0325671 to Abunassar et al., the entirety of the contents of each of these patents and published applications is incorporated herein by reference.

Variations in patient conditions and anatomies can result in leaflet thicknesses varying from relatively thin (e.g., tricuspid leaflets) to relatively thick (e.g., myxotamous thickened mitral valve leaflets). It therefore would be beneficial to provide a leaflet coaptation fixation device to accommodate a range of tissue thickness to increase procedural ease and reduce the likelihood of tissue injury. The disclosed subject matter of herein is directed to a variety of fixation device configurations, features and aspects that enable the treatment of thin and/or thick leaflets, or both, simultaneously. The features and aspects disclosed herein can be incorporated and combined into a variety of tailored fixation device configurations. Furthermore, if desired, a specific design can be specified by a user to enable the safe and easy treatment of a specific valve being evaluated.

Transcatheter (e.g., trans-septal) edge-to-edge valve repair has been established using a fixation device. These fixation devices are configured to enhance coaptation between opposing leaflets. Such fixation devices generally include two types of leaflet contacting design elements. The first element is a sub-valvular arm also known as a fixation element, configured to contact the ventricular side of a leaflet to be grasped. Once the arms are positioned to stabilize the leaflet in a beating heart, a second element known as a gripping element or proximal element can be lowered into contact with the atrial side of the leaflet to capture the leaflet. Once two opposing leaflets are captured, each between a respective arm or gripping element, the fixation device can be closed with the arms raised or moved reduce the arms angle such that the leaflets are brought into coaptation, which results in a reduction in valvular regurgitation during ventricular systole.

During this procedure, a fixation device design can utilize a single, central, fixed axis to rotate both the arms (i.e., ventricular contacting elements) and gripping elements (i.e., atrial capture elements), respectfully, to secure leaflets within the fixation device. However, leaflet thickness and characteristics can vary greatly from one patient to another, and even within a single valve. For example, mitral and tricuspid leaflets typically can be thicker at their outermost edge, which is adjacent to a thinner, more central belly region.

The thickness of leaflets being grasped and captured within a fixation device can vary by valve type and by disease state. For purpose of illustration and not limitation, a commonly treated mitral valve can have leaflets between 0.8 and 2.0 mm thick, however, the thickness of leaflets can vary due to a variety of conditions. For example, leaflet thickness can vary significantly between the anterior mitral leaflet (AML) and the posterior mitral leaflet (PML). Additionally, a patient with a history of rheumatic fever can have leaflets that have thickened up to or beyond 5 mm (Saxena A, Echocardiographic Diagnosis of Chronic Rheumatic Valvular Lesions, Global Heart Volume 8, Issue 3, September 2013, pgs. 203-212). By contrast, tricuspid valve leaflets can be thinner than those of the mitral valve, with a thickness between 0.8 and 1.1 mm (Silver et al., Morphology of the Human Tricuspid Valve, Circulation, Volume XLIII, March 1971). Furthermore, certain leaflet regions can be relatively thicker (i.e., rough zones) proximate their free edges and at chordae attachment zones, whereas leaflets can be relatively thin near the ventral belly region (Pham et al., Material Properties of Aged Human Mitral Valve Leaflets, J Biomed Mater Res A. 2014 August; 102(8): 2692-2703).

To address these various leaflet parameters, a fixation device is disclosed herein with improved configurations for enhanced performance with regard to device and tissue interaction. For example, since leaflet thickness is known to vary, this disclosure describes a fixation device design for effectively treating a range of known valve thicknesses. Additionally, the various features and aspects as described herein can be combined as desired to provide a tailored fixation device for a desired valve configuration.

Generally, and as set forth in greater detail below, the disclosed subject matter provided herein includes a fixation device for fixation of leaflets of a heart valve. The fixation device generally includes a central member defining a longitudinal axis of the fixation device, and first and second arms rotatable about at least one arm hinge point between an open position and a closed position. The fixation device further includes a first gripping element rotatable about a first gripping element axis of rotation to capture a first leaflet of a heart valve between the first gripping element and the first arm. The fixation device further includes a second gripping element rotatable about a second gripping element axis of rotation to capture a second leaflet of a heart valve between the second gripping element and the second arm. In accordance with the disclosed subject matter, at least one of the first gripping element axis of rotation and the second gripping element axis of rotation is variably offset from the arm hinge point by an axis offset distance defined along the longitudinal axis.

Referring to FIG. 1, for purpose of illustration and not limitation, a fixation device 104 for fixation of leaflets of a heart valve includes an elongate central member 111 defining a longitudinal axis 105 of the fixation device 104 and first and second arms 108, 110 rotatable about at least one arm hinge point 122 between an open position and a closed position. For purpose of illustration and not limitation, an exemplary open position is depicted in FIG. 1. In the open position, tissue capture can occur wherein a respective arm is disposed to engage a ventricular side of a native leaflet. In accordance with the disclosed subject matter, the arms 108, 110 each can have a concave shape configured to allow a gripping element and target leaflets to be nested or recessed within the respective arm. A concave shape can increase the surface area of the leaflets engaged by the arms 108, 110 and create a geometry of leaflet engagement for an improved retention force. Each arm 108, 110 can be a single structure, or comprised of multiple components. For example, the multiple components can include a metal or wire frame surrounded by a cover, such as a fabric or other flexible material as to enhance grip and tissue ingrowth following implantation.

The fixation device of FIG. 1 further includes a first gripping element 116 rotatable about a first gripping element axis of rotation 127 to capture a first leaflet of a heart valve 112 between the first gripping element 116 and the first arm 108. Additionally, the fixation device includes a second gripping element 118 rotatable about a second gripping element axis of rotation 129 to capture a second leaflet of a heart valve 114 between the second gripping element 118 and the second arm 110. The gripping elements 116, 118 and the arms 108, 110 each can include friction-enhancing features such as barbs, bumps, grooves, openings, channels, surface roughening, coverings, and coatings, among others. The friction-enhancing features can be configured to increase the retention force of the fixation and gripping elements on leaflets, without significant injury or scarring to the leaflet if the fixation device is removed.

With continued reference to FIG. 1, and in accordance with the disclosed subject matter, at least one of the first gripping element axis of rotation 127 and the second gripping element axis of rotation 129 is variably offset from the arm hinge point 122 by an axis offset 106 distance defined along the longitudinal axis 105. The axis offset 106 can be adjusted to accommodate a corresponding leaflet thickness by the fixation device 104. Additionally, with an axis offset, focal tissue injury at the tip of a leaflet and leaflet ejection can be reduced during leaflet grasping and capture.

Further in accordance with the disclosed subject matter, and as depicted in FIG. 1 for illustration and not limitation, the first gripping element 116 and the second gripping element 118 can be operatively coupled together whereby the first gripping element axis of rotation 127 and the second gripping element axis of rotation 129 define a single axis of rotation. Alternatively, and as described in detail below, the first and second gripping elements 116, 118 each can have separate axis of rotation 127, 129, which can be variably offset independently or together.

As embodied herein, and as further depicted in FIG. 1, at least one of the first gripping element axis of rotation 127 and the second gripping element axis of rotation 129 can be biased toward the at least one arm hinge point 122 for automatic adjustment of the axis offset distance 106 upon capture of a native leaflet. For example, and as depicted herein, the first gripping element axis of rotation 127 and the second gripping element axis of rotation 129 form a single axis of rotation, which can be biased by a spring 148 operatively connected to a location proximate the arm hinge point 122. The spring 148 can be attached to the gripping elements using a pin element, or the like, configured to allow travel in a channel or similar guide (not shown) within the elongate central member 111 toward the arm hinge point 122. The spring 148 element, or similar biasing mechanism, thus allows for automatic adjustment of the axis offset 106 based upon the thickness of the captured leaflet. For the purpose of illustration and not limitation an exemplary embodiment of the spring 148 can provide a maximum amount of resistance of around 0.02 to 0.20 pounds-force (lbf), to minimize the likelihood of leaflet trauma, while still allowing for capture. A preferred range can be 0.05 to 0.16 lbf when measured at a lever arm distance of 5 to 8 mm along the gripping element 116, 118 length. The spring 148 also can function to allow the first and second gripping elements axis of rotation 127, 129 to adjust upward and downward relative the arm hinge point 122. Additionally, the spring can be provided with a tunable spring force, such as by an adjustment screw or the like. Although shown with the spring aligned along the longitudinal axis of the central member, the spring can be oriented in different oblique configurations using corresponding slots or guides in the elongate central member 111. In exemplary configurations, the spring 148 can bias the first and second gripping element axes of rotation 127, 129 toward the arm hinge point 122. Compression of the spring 148 can decrease the axis offset 106 and expansion of the spring 148 (e.g., during leaflet capture) can increase the axis offset 106.

Additionally, FIG. 1 depicts a single spring 148 for automatic adjustment of both the first and second gripping elements axes of rotation 127, 129, but it is recognized that a separate spring can be provided for automatic adjustment of each gripping element axis of rotation independently, as desired. Each spring 148 can be selectable and replaceable by the user in this manner. Each spring 148 can be configured to accommodate a full range of leaflet thicknesses. Alternatively, each spring 148 can be designed for a particular range of leaflet thicknesses and the spring 148 can be selectable based on its desired parameters. For example, the spring can be selected after an analysis of the patient's leaflets is performed. In some circumstances, a more compliant spring can be used to treat a relatively delicate leaflet in a patient having, for example, advanced age and severe congestive heart failure. Further, a selectable spring force can be combined with other selectable parameters disclosed herein, such as a selectable offset distance.

Further in accordance with the disclosed subject matter, at least one of the first gripping element axis of rotation 127 and the second gripping element axis of rotation 129 can be located at an end of the respective gripper element 116, 118 proximate the elongate central member 111, as depicted in FIGS. 1-3 and 12-16. That is, for illustration and not limitation, each of the first gripping element 116 and the second gripping element 118 can be operatively coupled to the elongate central member 111, such as by a pivot point or hinge, as shown in FIGS. 1-8 and 12-16. As embodied herein, and as illustrated in FIGS. 1, 3, 5, 7, 9, 10, and 11, each of the first gripping element axis of rotation 127 and the second gripping element axis of rotation 129 can be variably offset from the arm hinge point 122 directly by movement of the respective hinge. Further, and as depicted in FIGS. 2-7, and as described further below in accordance with another aspect of the disclosed subject matter, the axis offset distance 106 between the at least one hinge point 122 and the at least one of the first gripping element axis of rotation 127 and the second gripping element axis of rotation 129 can be incrementally selectable.

In accordance with another aspect of the disclosed subject matter, the fixation device 104 can include selectable offsets wherein a user can select or configure the fixation device 104 to the desired parameters before introduction into the body. For example, if a user is treating a patient valve with relatively thin leaflets (e.g., 0.5 mm-0.8 mm), the user can adjust the axis offset by lowering one or both connector pins 142 toward the arm hinge point such that thin leaflets are secured reliably during the procedure with reduced risk of local injury. Similarly, if a user is intending to treat a myxotamous or rheumatic patient valve with exceptionally thick leaflets (e.g., to 5 mm or 6 mm), the user can adjust the axis offset by moving the connector pins 142 away from the arm hinge point such that the fixation device is tailored to thicker leaflets. Selectable offset can include a single fixation device capable of being reconfigurable by the user (e.g., with a retaining pin). Additionally or alternatively, a plurality of fixation devices 104 can be provided in a kit wherein different fixation devices are provided with differing parameters wherein a selected device is chosen for a given leaflet parameters. A combination of the two is also contemplated. For user-selectable offsets, pre-procedural imaging can be performed to determine leaflet parameters.

In accordance with the disclosed subject matter, the fixation device 104 can include an individual, independent axis offset for each gripping element to facilitate differing leaflet thicknesses for an opposing anterior mitral leaflet (AML) and posterior mitral leaflet (PML). Individual offsets can be beneficial if prior to surgery a very thick AML (e.g., 4 mm) is observed through imaging while a thin PML (e.g., 1 mm) is observed. In this example, an offset of 4 mm can be selected by the user for one side of the fixation device 104 and a 1 mm offset can be selected for the other side of the fixation device 104.

With reference now to FIGS. 2, 4, 6, and 12-16, one gripping element is shown for purpose of illustration and clarity, however, it is understood that the fixation device 104 would include more than one gripping element. The second gripping element can be of the same configuration as the first, or another embodiment as disclosed can be used in combination.

Figure 2:
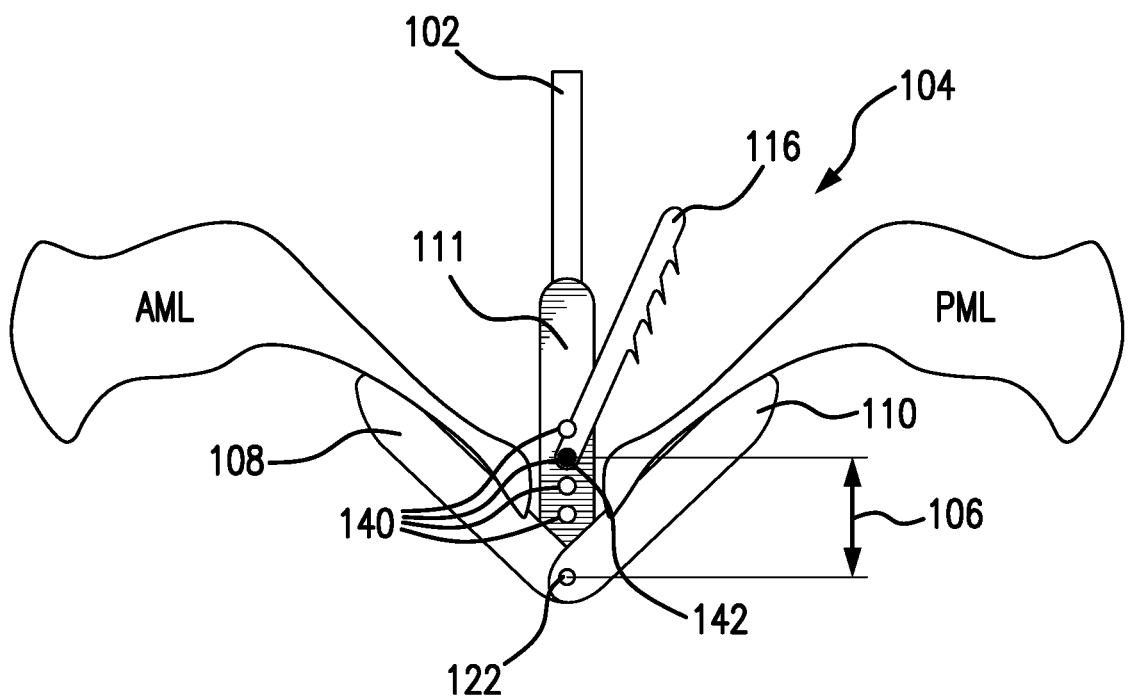
FIG. 2 is a front schematic view of an alternative embodiment of a portion of a fixation device in accordance with the disclosed subject matter.
Figure 3:
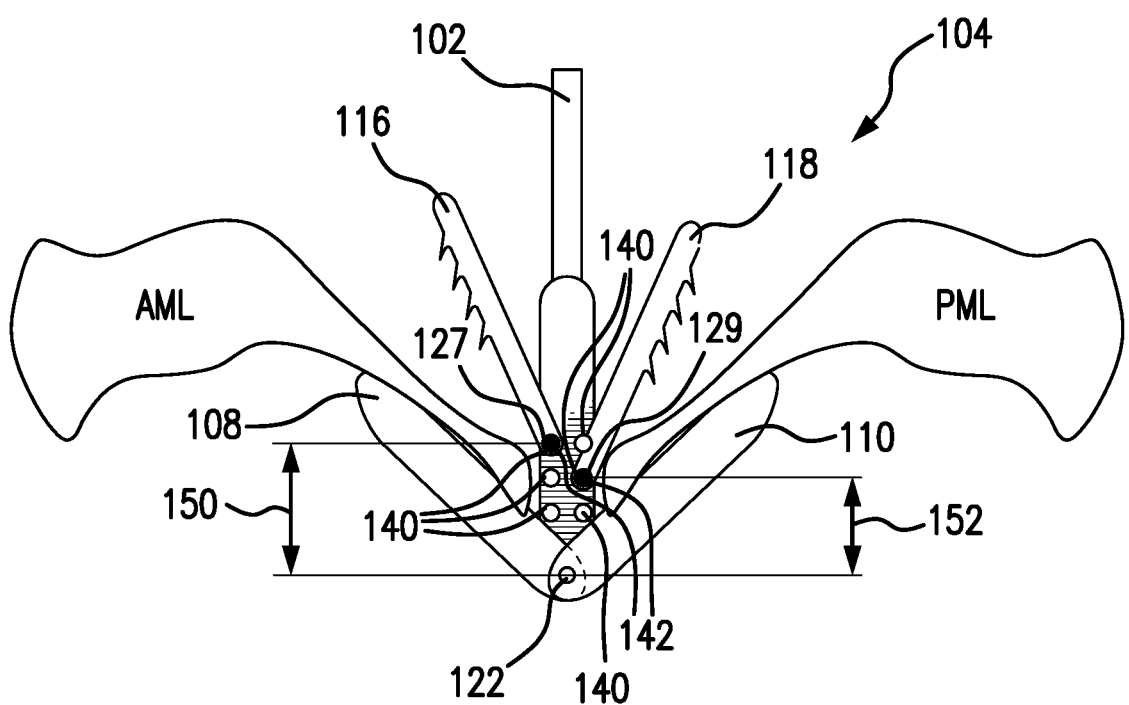
FIG. 3 is a front schematic view of another exemplary embodiment of a fixation device in accordance with the disclosed subject matter.
Figure 4:
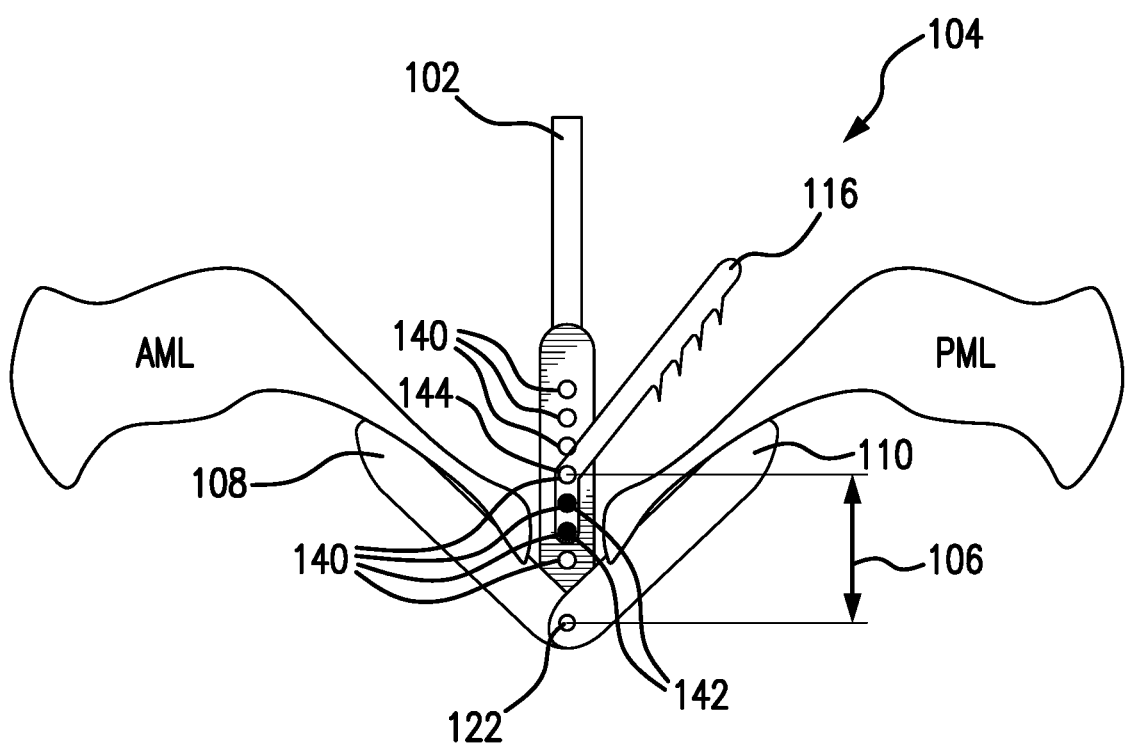
FIG. 4 is a front schematic view of an alternative exemplary embodiment of a portion of a fixation device in accordance with the disclosed subject matter.
Figure 5:
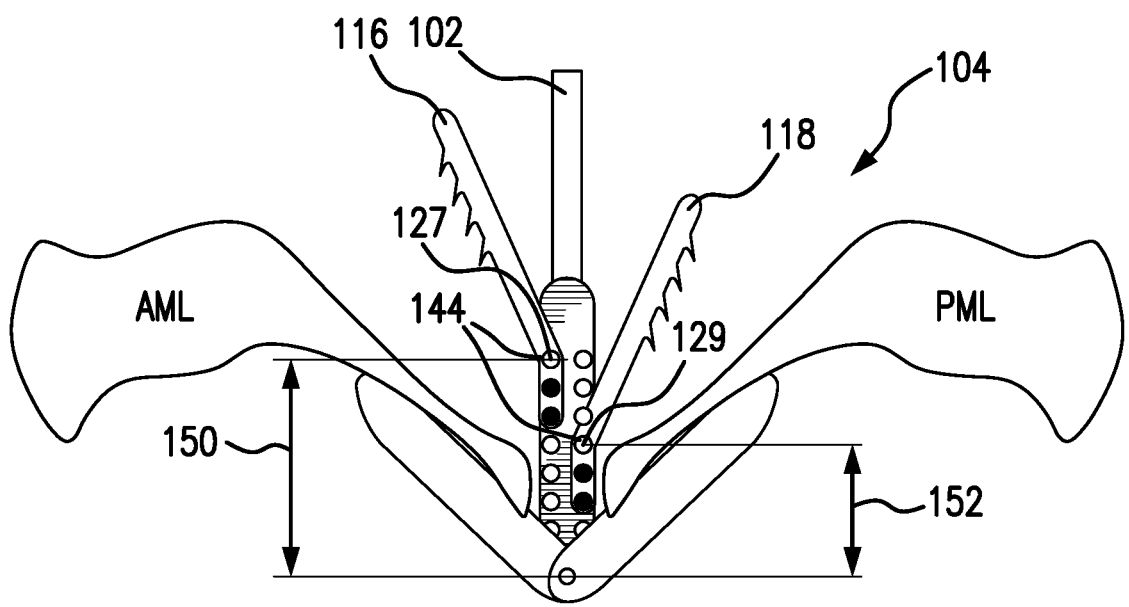
FIG. 5 is a front schematic view of another exemplary embodiment of a fixation device in accordance with the disclosed subject matter.

As depicted in FIG. 2, and in accordance with a further aspect of the disclosed subject matter, the at least one of the first gripping element axis of rotation 127 and the second gripping element axis of rotation 129 each can include at least one connector pin 142, and the elongate central member can include a plurality of pin holes 140 defined therein and configured to engage with the connector pin 142, as also shown in FIGS. 3-5. As illustrated herein, the pin holes 140 can be spaced longitudinally along the elongate central member 111. The connector pin 142 can be any type of pin (e.g., a codder pin) or similar component insertable by a user to select the desired axis offset. Similarly, the pin and pin holes can be in the form of a ratchet and pawl rack, or other mechanical engagement configuration, to allow incremental selection along a range of dimensions.

Figure 7:
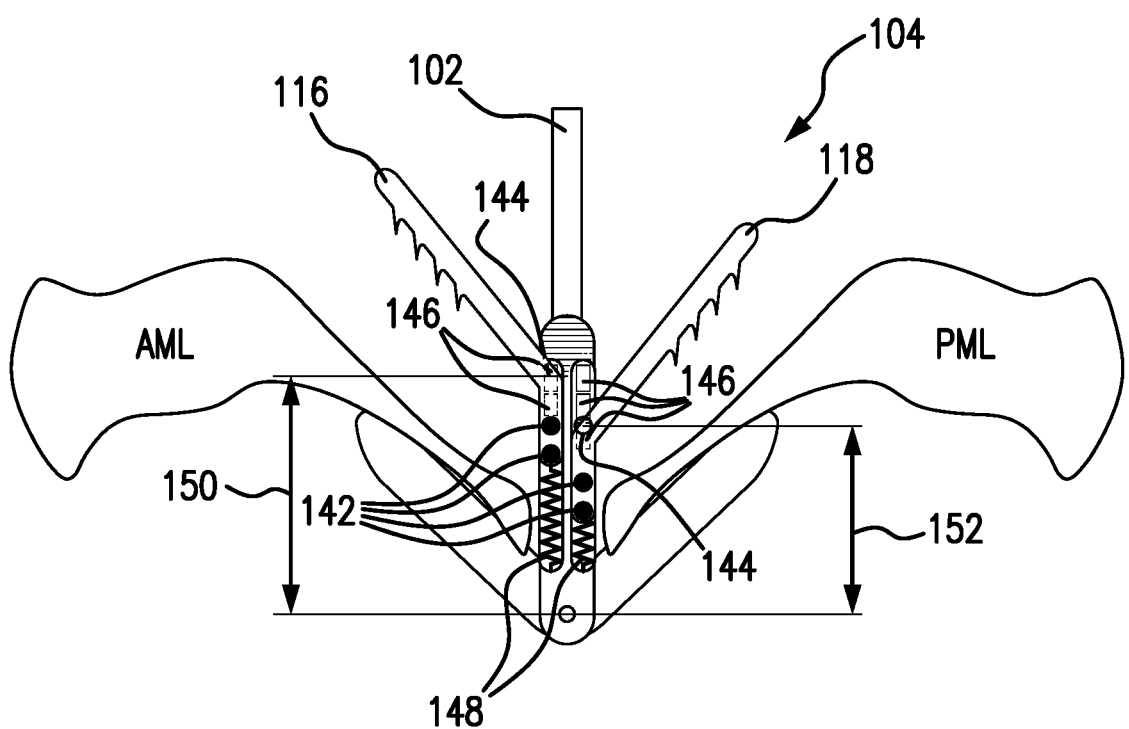
FIG. 7 is a front schematic view of another exemplary embodiment of a fixation device in accordance with the disclosed subject matter.

Referring now to FIG. 3, and in accordance with a further aspect of the disclosed subject matter, the first gripping element axis of rotation 127 can be parallel to and spaced along the longitudinal axis 105 from the second gripping element axis of rotation 129, as also depicted in FIGS. 5 and 7. As previously noted, each of the first gripping element axis of rotation 127 and the second gripping element axis of rotation 129 can be variably offset from the arm hinge point 122. In this manner, a first offset distance 150 can be defined between the arm hinge point 122 and the first gripping element axis of rotation 127, and a second offset distance 152 can be defined between arm hinge point 122 and the second gripping element axis of rotation 129. In accordance with a further aspect of the disclosed subject matter, and as depicted in FIGS. 3, 5, 7, and 9-11, selection of the first offset distance 150 can be independent of the second offset distance 152.

As previously noted, and as depicted in FIGS. 2 and 3, at least one of the first and second gripping elements axes of rotation can be located at an end of the respective gripping element, such as by the pivot point. Alternatively, and with reference now to FIG. 4, in a still further aspect of the disclosed subject matter, the at least one of the first gripping element axis of rotation 127 and the second gripping element axis of rotation 129 can be a flex portion 144 defined along a length of the respective gripping element 116, 118, as also depicted in FIGS. 5, 6, and 8-11. The flex portion can be in the form of a living hinge along the length of the of the gripping element such as by a reduced cross-dimension or altered characteristic to allow flexion at a desired location. For purpose of illustration and not limitation, the respective gripping element 116, 118 having the flex portion 144 can be attached to the elongate central member 111, as shown in FIGS. 4-8, and 10. Alternatively, the respective gripping element 116, 118 having the flex portion 144 can be attached to a corresponding one of the first and second arms 108, 110, as depicted in FIGS. 9 and 11.

Referring back to FIG. 4, and in accordance with another aspect of the disclosed subject matter, more than one pin can be used per gripping element to secure one end of the gripping element such that the gripping elements can bend at the flex portions. As embodied herein, the flex portions can be configured to bias the gripping element toward the respective arm. The bias can be achieved with a variety of manufacturing techniques, such as inducing an internal strain, or if a shape memory material is used, by treating the material, e.g., by a process including repeated heating, bending, and cooling of the gripping elements.

Figure 6:
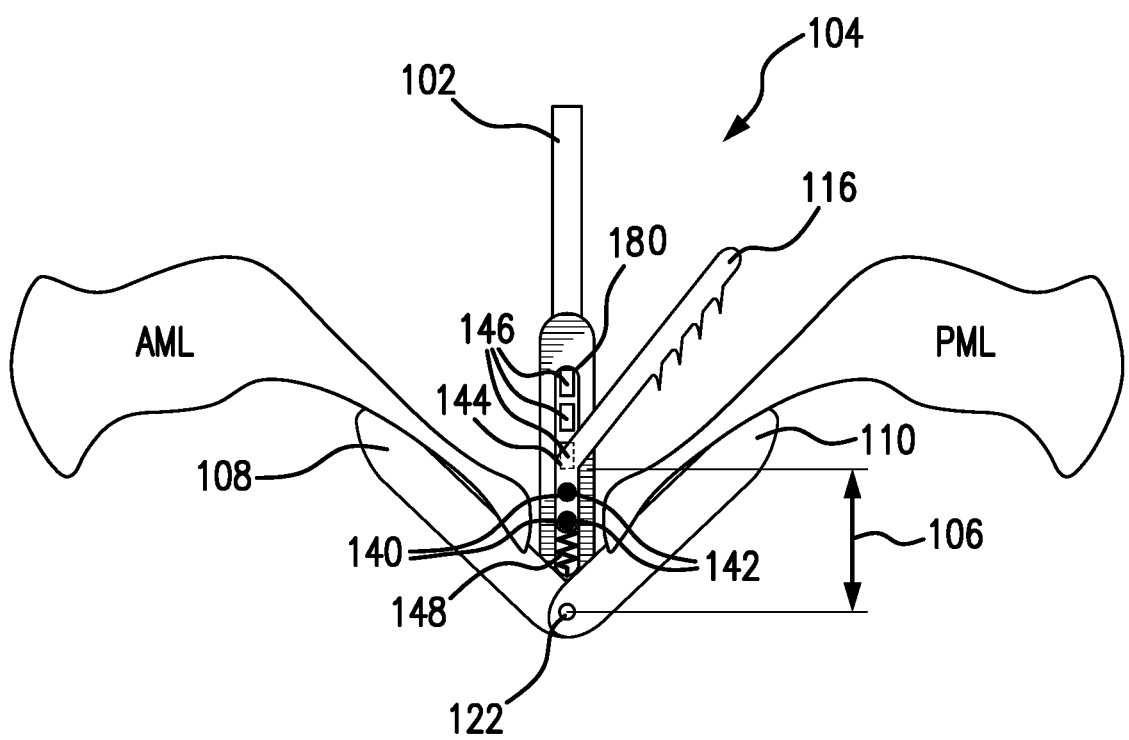
FIG. 6 is a front schematic view of another alternative exemplary embodiment of a portion of a fixation device in accordance with the disclosed subject matter.

Referring now to FIGS. 6 and 7, and in accordance with yet another aspect of the disclosed subject matter, at least one of the first gripping element axis of rotation 116 and the second gripping element axis of rotation 118 can be biased away from the at least one arm hinge point 122, and at least one shim 146 can be provided to limit the maximum axis offset distance 106. That is, the axis of the offset distance can be incrementally selected by the dimension of the shim selected. As depicted, for purpose of illustration and not limitation, the bias can be caused by a spring 148 acting upon an end of the gripping element. A single spring can be configured to act on one or both gripping elements, or a separate spring can be configured for independent movement of each gripping element, respectively (see FIG. 7) With continued reference to FIGS. 6 and 7, and in accordance with a further aspect of the disclosed subject matter, at least one of the first gripping element axis of rotation 127 and the second gripping element axis of rotation 129 can be variably adjustable along a channel 180 or similar guide defined in the elongated central member 111, the device further including at least one shim 146 disposed in the channel 180 to limit maximum axis offset distance 106. The shims 146 can be inserted by the user prior to surgery, wherein additional shims further limit the maximum axis offset or pre-installed as part of a kit of other devices with differing maximum axis offset distance. In an exemplary embodiment, tapered shims of suitable material of construction, e.g., a metal or composite, can be used, although similar mechanisms can be used to limit the maximum axis offset.

Figure 8:
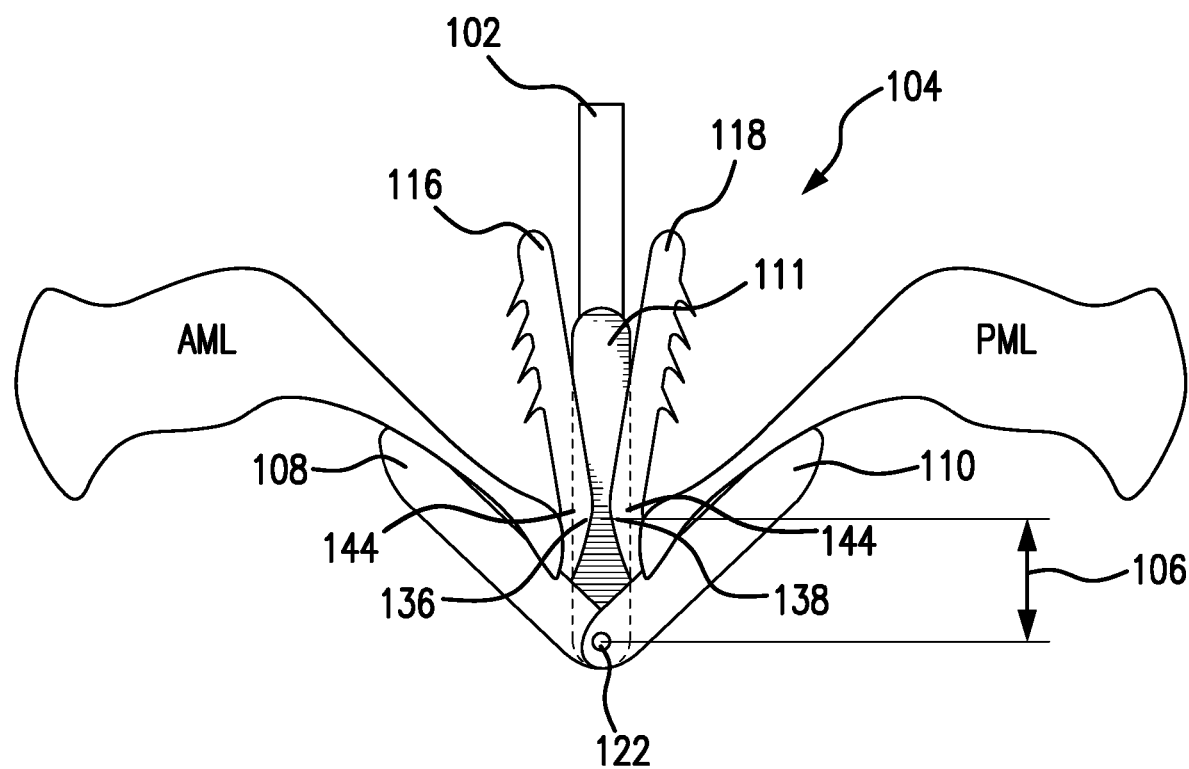
FIG. 8 is a front schematic view of yet another alternative exemplary embodiment of a fixation device in accordance with the disclosed subject matter.
Figure 9:
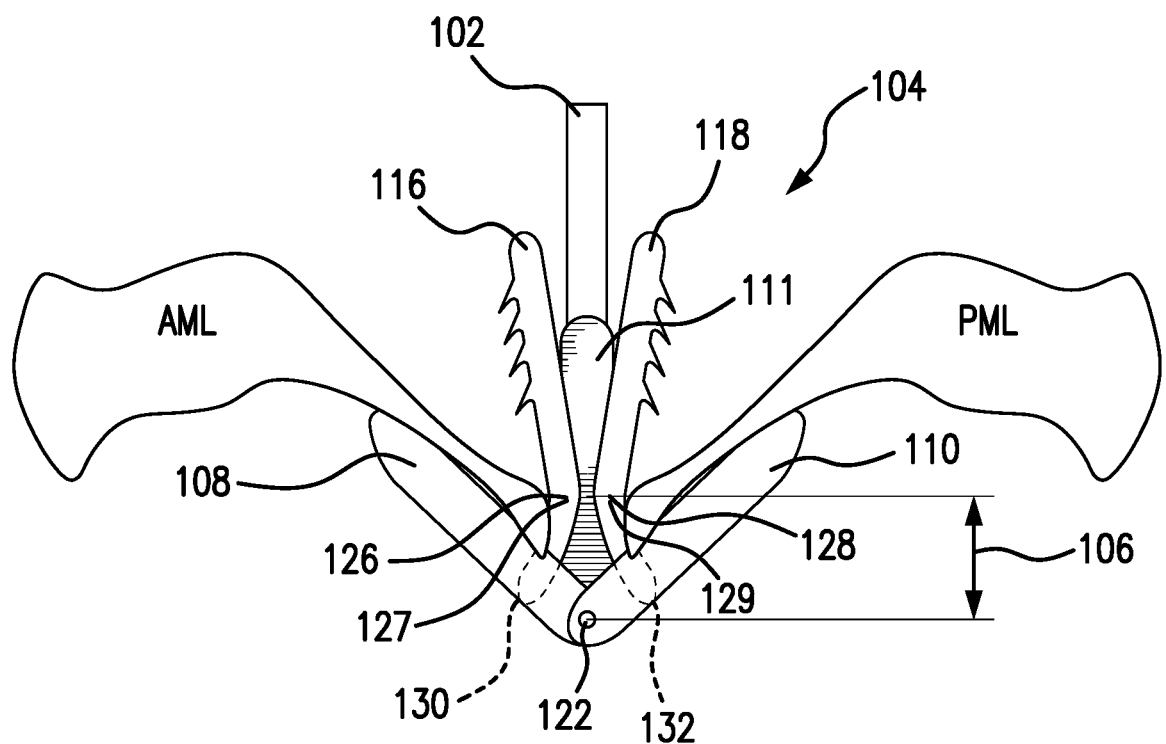
FIG. 9 is a front schematic view of another alternative embodiment of a fixation device in accordance with the disclosed subject matter.

With reference to FIG. 8, and for purpose of illustration and not limitation, the fixation device 104 can comprise the first gripping element 116 secured directly to the elongate central member 111 at a first connection point 136, and likewise the second gripping element 118 secured directly to the elongate central member 111 at a second connection point 138 wherein at least one gripping element 116, 118 can include a flex portion 144 configured to allow for a variable offset of the gripping element axis of rotation 127, 129. The flex portion can enable a degree variable offset, rather than a defined axis, and thus enables the gripping element axis of rotation 127, 129 to self-adjust to leaflet characteristics. The gripping elements 116, 118 with the flex portion 144 can be securely attached to the central portion using any variety of connection means. Alternatively, the gripping element can be attached to a respective arm, as depicted in FIG. 9.

Figure 10:
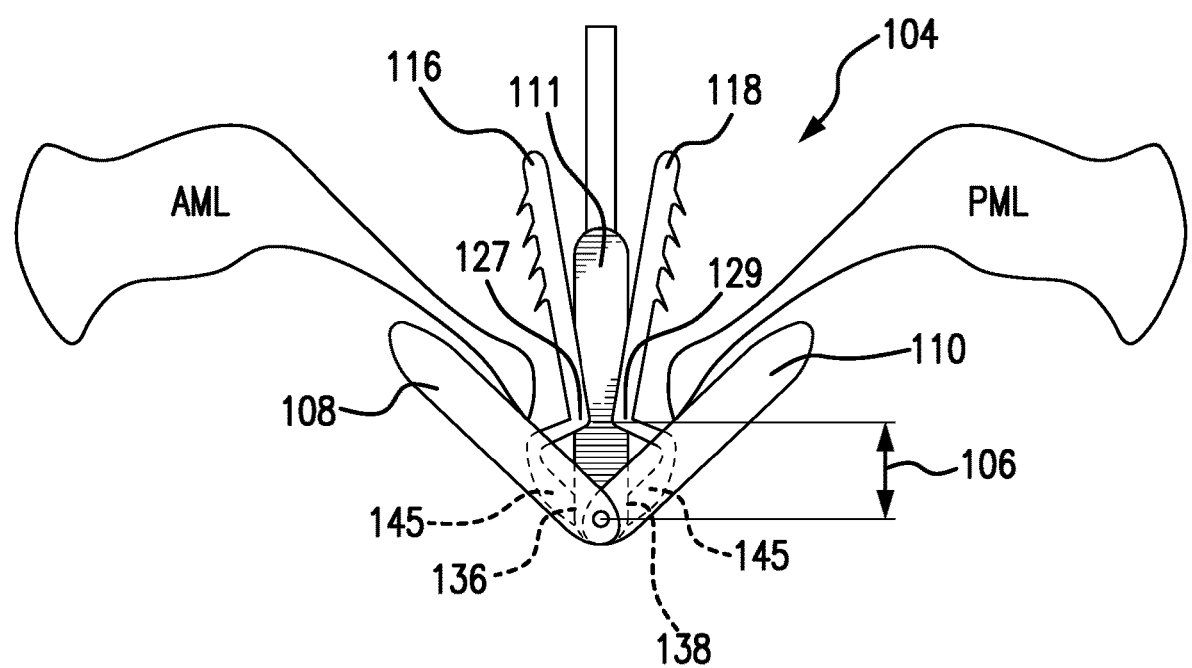
FIG. 10 is a front schematic view of an additional alternative exemplary embodiment of a fixation device in accordance with the disclosed subject matter.
Figure 11:
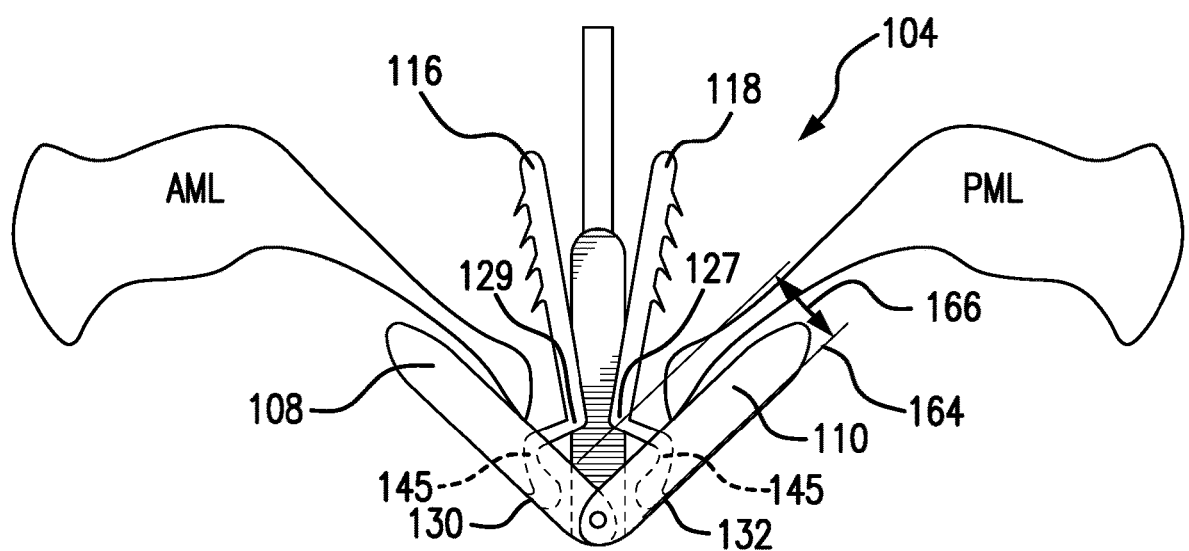
FIG. 11 is a front schematic view of another exemplary embodiment of a fixation device in accordance with the disclosed subject matter.

With reference to FIGS. 10 and 11, and in accordance with another aspect of the disclosed subject matter, at least one of the first gripping element axis of rotation 127 and the second gripping element axis of rotation 129 can alternatively be a compliant hinge 145 configured to variably change depending on a thickness of a captured native leaflet of the heart valve. A compliant hinge 145 can allow the axis offset 106 to be shifted when thicker tissue is present within the fixation device. Similar to the flex portion 144 described above, which enables a degree of variable offset, a compliant hinge 145 has multiple hinges in a zig-zag configuration to enable the gripping element 116, 118 to elongate and generally enable a higher degree of variable offset than the flex portion 144.

As with previous aspects of the disclosed subject matter, the gripping element 116, 118 having the compliant hinge 145 can be coupled to the elongate central member 111, as shown in FIG. 10. Alternatively, the gripping element 116, 118 having the compliant hinge 145 can be coupled to the corresponding arm 108, 110, as depicted in FIG. 11. Gripping elements 116, 118 attached to the arms 108, 110 (as also shown in FIG. 9) have a gripping element axis of rotation 127, 129 that shifts away from the hinge point 122 as the arms close and shifts towards the hinge point 122 as the arms open. Attachment of the gripping element 116, 118 to the corresponding arm 108, 110 enables gripping to be performed at additional clip arm angles, which can be useful in capturing leaflets having high mobility, large gap, or challenging geometric leaflet angles. As depicted, an arm reference plane 164 can be defined by a length of a distal side of the arms. An arm axis offset 166 can be defined by the distance between the arm reference plane 164 and a corresponding gripping element axis of rotation 127, 129.

Referring now to FIGS. 12-16, and in accordance with still another aspect of the disclosed subject matter, at least one arm 108, 110 can include a trough 154 having a trough bottom defining a trough reference plane 162, and further wherein the arm hinge point 122 can be offset from the trough reference plane by a trough offset distance 107 defined along the longitudinal axis 105. As embodied herein, the trough can be a depression extending into a surface of an arm 108, 110. The trough can extend substantially the entire length of the arm, as depicted for illustration in FIGS. 12-14, or in a select portion of the arm, as depicted for illustration in FIGS. 15 and 16. The trough 154 can be used in combination with any of the embodiments of the disclosed subject matter.

Figure 12:
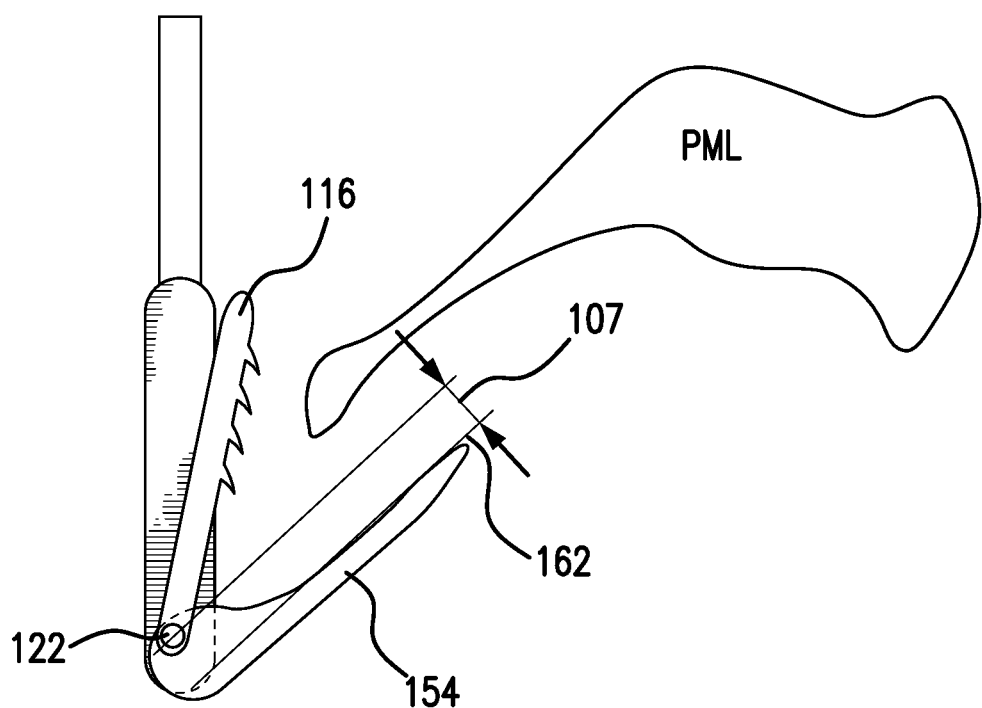
FIG. 12 is a front schematic view of an exemplary embodiment of a portion of a fixation device with an additional aspect in accordance with the disclosed subject matter.
Figure 13:
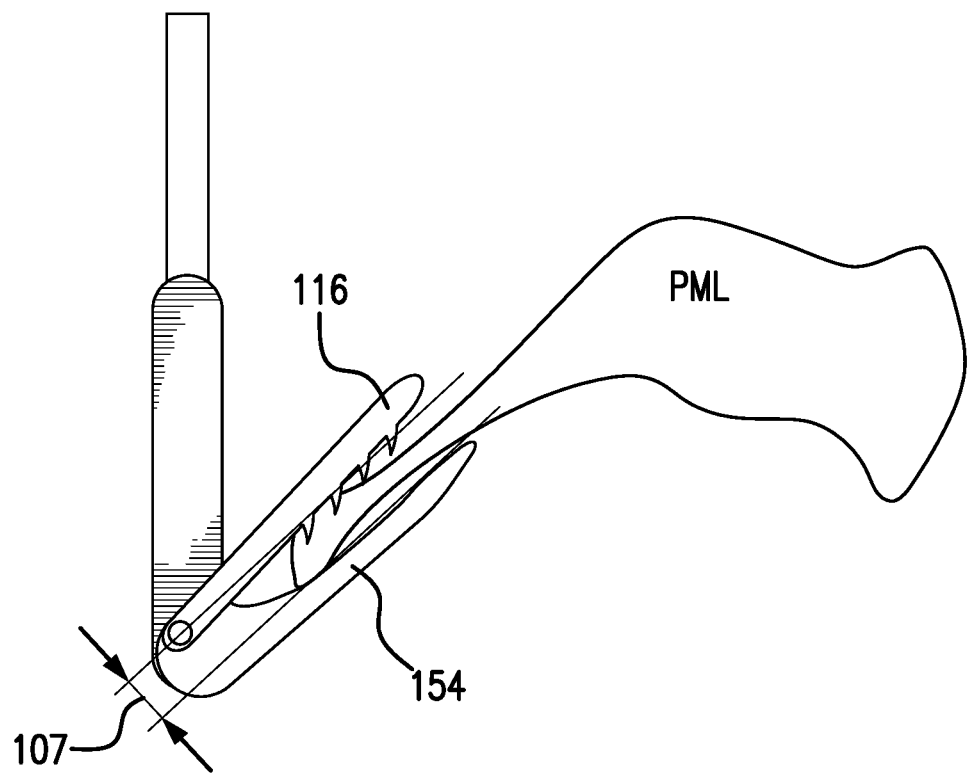
FIG. 13 is a front schematic view of the exemplary embodiment of FIG. 12 in a closed position.
Figure 14:
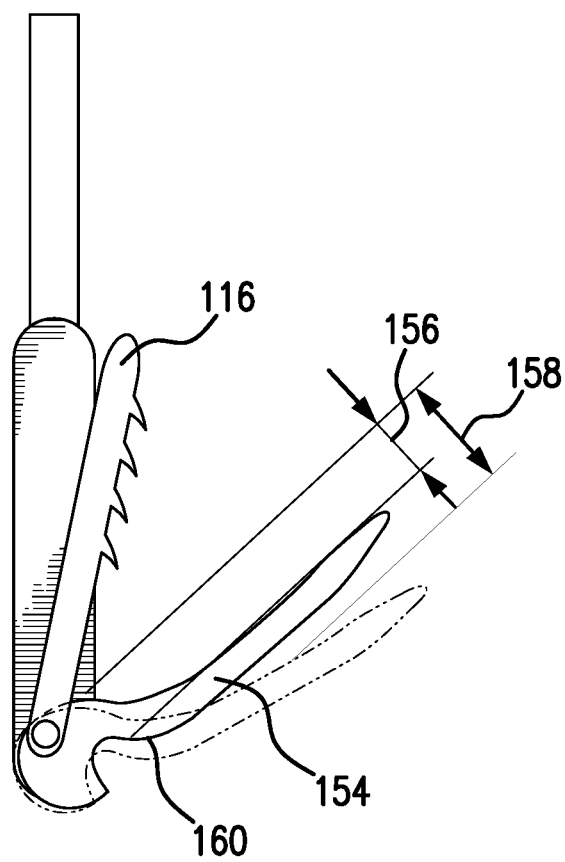
FIG. 14 is a front schematic view of an alternative exemplary embodiment of a portion of a fixation device in accordance with the disclosed subject matter.

For purpose of illustration and not limitation, the embodiment of FIG. 12 includes an arm having a trough with the fixation device configured to capture tissue, and FIG. 13 illustrates an arm having a trough with a fixation device configured with a leaflet successfully captured therein. A trough offset 107 can be fixed and unalterable, as depicted in FIGS. 12 and 13. Such fixed configuration can be used in combination with the kit concept previously described herein. Additionally or alternatively, the trough can be combined with the variable offset gripping element axis of rotation, as described above. Furthermore, with reference to FIG. 14, a fixation device 104 having a trough offset 107 can be incorporated into a flexible arm having an arm flexion portion 160 configured to dynamically adjust the trough offset as tissue is compressed therein. For example, a relatively small trough offset 156 can accommodate relatively thin tissue, and a relatively large trough offset 158 can accommodate relatively thick tissue. A flexible and compressible pad (not shown) can also be included in the trough.

Figure 15:
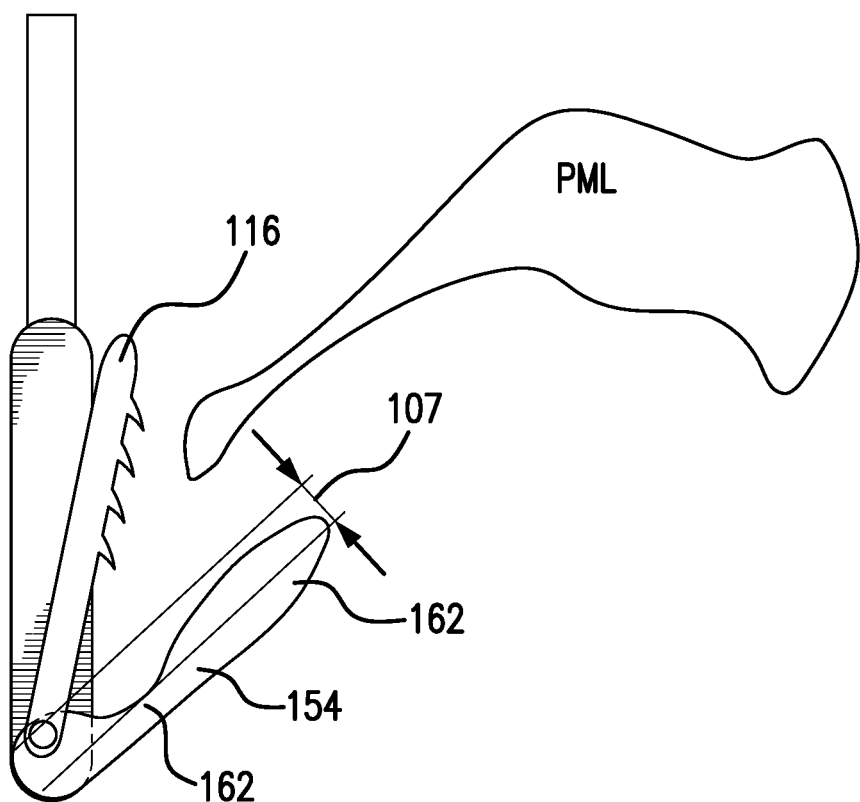
FIG. 15 is a front schematic view of another alternative exemplary embodiment of a portion of a fixation device in accordance with the disclosed subject matter.
Figure 16:
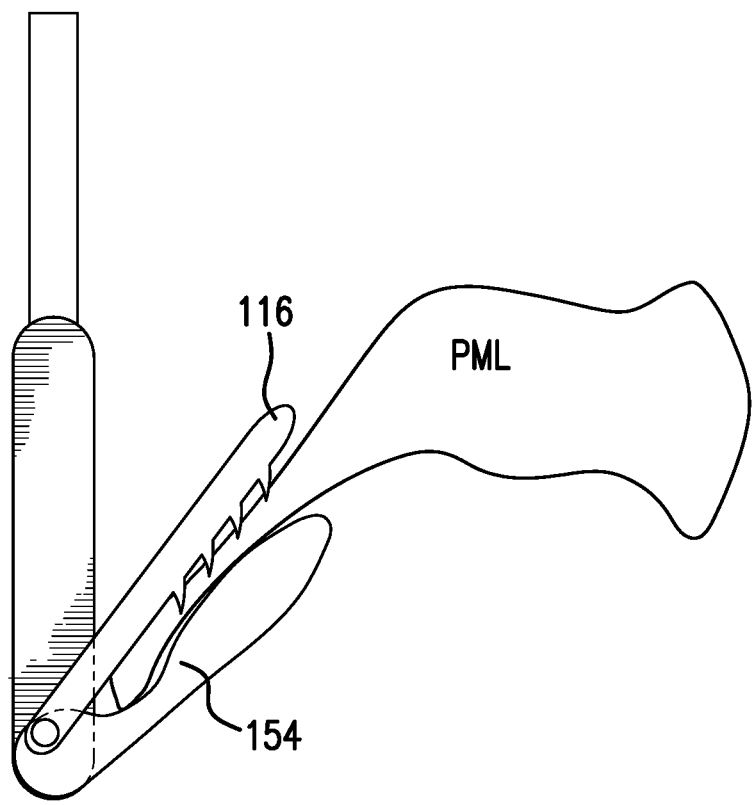
FIG. 16 is a front schematic view of the exemplary embodiment of FIG. 15 in a closed position.

With reference now to FIGS. 15 and 16, another exemplary embodiment of a portion of a fixation device in accordance with the disclosed subject matter is depicted having a trough 154 depression that varies along the length of the arm. For example, a trough 154 can include a portion with a larger depression proximate the elongate central member 111 where the tip of a leaflet can be positioned, and a smaller depression proximate a free end of the arm where the belly of a leaflet can be positioned. A trough 154 having a varied depression can result in a more uniform and similar contact force along the length of an inserted leaflet and can reduce tissue injury. Further, a trough 154 having a varied depression can aid in temporarily securing leaflets during grasping. For purpose of illustration and not limitation, FIG. 15 illustrates a fixation device configured to capture tissue, and FIG. 16 illustrates a fixation device configured with a leaflet successfully captured therein.

For purpose of illustration and clarity, FIGS. 12-16 can represent only a portion of a fixation device and additional elements of a fixation device, such as a second arm and a second gripping element etc., can be included having similar features to those shown herein. In accordance with the disclosed subject matter, the various trough configurations can be combined with any of the other aspects of the fixation device disclosed herein, such as the variable axis offset embodiments.

Figure 17:
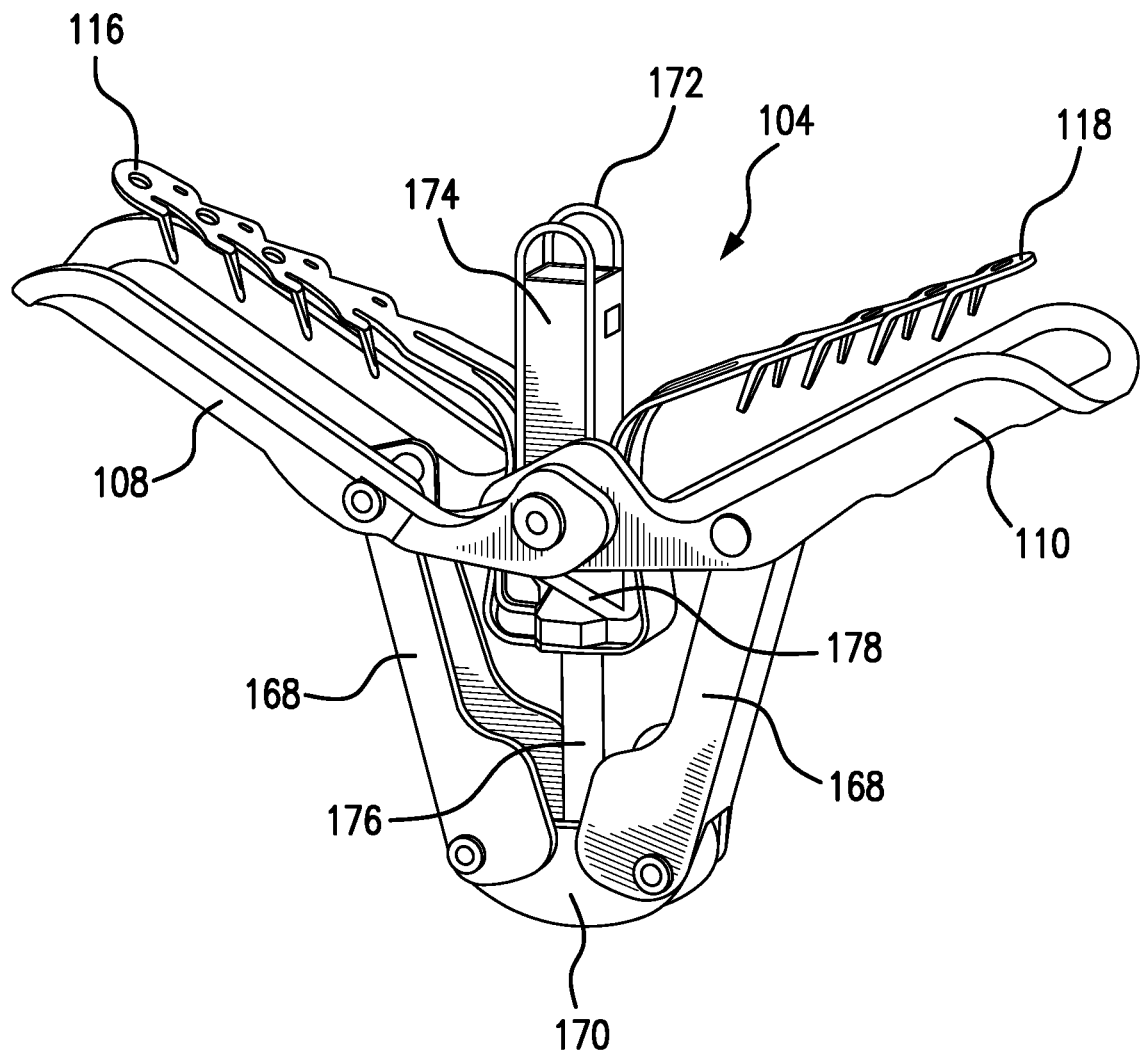
FIG. 17 is a perspective view of an exemplary embodiment of a fixation device, which can be modified to include one or more aspects in accordance with the disclosed subject matter.

Further in accordance with the disclosed subject matter, various components and operation of the fixation device 104 in accordance with the disclosed subject matter can be substituted with, or used in combination with, numerous alternative or additional components and operations, such as the components depicted in FIG. 17. For example, each arm 108, 110 can have a cupped or concave configuration, as depicted, to surround a portion of the fixation device 104 and optionally contact each other on opposite sides of the device. Further, each gripping element 116, 118 can be biased toward each respective arm 108, 110. Prior to leaflet capture, each gripping element 116, 118 can be moved inwardly toward a longitudinal center of the device (i.e., away from each respective arm 108, 110) and held with the aid of one or more gripper element lines (not shown) which can be in the form of sutures, wires, nitinol wire, rods, cables, polymeric lines, or other suitable structures. The sutures can be operatively connected with the gripping elements 116, 118 in a variety of ways, such as by being threaded through loops disposed on the gripping elements 116, 118.

The fixation device 104 can further include two link members or legs 168, each leg 168 having a first end which is rotatably joined with one of the arms 108, 110 and a second end which is rotatably joined with a base 170. The base 170 can be operatively connected with a stud 176 which can be operatively attached to a distal end of a delivery shaft 102. In some embodiments, the stud 176 can be threaded so that the distal end of a delivery shaft 102 can attach to the stud 176 by a screw-type action. Further, the connection point between the stud 176 and the distal end of a delivery shaft 102 can be disposed within the coupling member 174. However, the distal end of a delivery shaft 102 and stud 176 can be operatively connected by any mechanism which is releasable to allow the fixation device 104 to be detached. The stud can be axially extendable and retractable to move the base and therefore the legs 168 which rotate the arms 108, 110 between closed, open and inverted positions. Likewise, immobilization of the stud, such as by a locking mechanism, can hold the legs 168 in place and therefore lock the arms 108, 110 in a desired position. Further details are disclosed in the patents and publications incorporated by reference herein.

In each of the embodiments disclosed herein, the fixation device 104 can be releasably coupled to the distal end of a delivery shaft 102.

The embodiments illustrated herein are adapted for repair of a heart valve, such as a mitral valve, using an antegrade approach from a patient's left atrium. For some embodiments (e.g., embodiments requiring user input) imaging can be performed prior to a procedure to anticipate a patient's tissue thickness and assist a user in selecting a fixation device having the desired parameters. After imaging, a user can select an appropriate fixation device 104 (e.g., from a kit, as described above). Additionally or alternatively, a user can adjust the parameters of a fixation device 104 (e.g., a user-selectable axis offset). The desired fixation device 104 can be introduced in a femoral vein and advanced through the inferior vena cava into the heart, across a penetration in the interatrial septum. For mitral valve repair, the fixation device 104 can be advanced through the mitral valve from the left atrium to the left ventricle. The arms 108, 110 can be oriented to be perpendicular to a line of coaptation and then positioned so that the arms 108, 110 contact the ventricular surface of the valve leaflets, thereby grasping the leaflets. The gripping elements 116, 118 can remain on the atrial side of the valve leaflets so that the leaflets lie between the gripping elements 116, 118 and the arms 108, 110. The fixation device 104 can be repeatedly manipulated to reposition the device so that the leaflets are properly grasped at a desired location. Repositioning is achieved with the fixation device 104 in the open position. In some circumstances, regurgitation of the valve can also be checked while the fixation device 104 is in the open position. If regurgitation is not satisfactorily reduced, the fixation device 104 can be repositioned and regurgitation checked again until the desired results are achieved.

Once the fixation device 104 has been positioned in a desired location relative to the valve leaflets, the leaflets can then be captured between the gripping elements 116, 118 and the arms 108, 110. At this time, the gripping elements 116, 118 can be lowered toward the arms 108, 110 so that the leaflets are held therebetween. The arms 108, 110 can be closed to an angle selectable by the user and locked to the prevent the arms 108, 110 from moving toward an open position. The fixation device 104 can then be detached from the distal end of the delivery shaft 102. After detachment, the repair of the leaflets or tissue can be observed by non-invasive visualization techniques, such as echocardiography, to ensure the desired outcome. If the repair is not desired, the fixation device 14 can be retrieved. If the repair is satisfactory, the gripper element lines can be disconnected and the fixation device can be released for implantation.

While the embodiments disclosed herein utilize a push-to-open, pull-to-close mechanism for opening and closing arms it should be understood that other suitable mechanisms can be used, such as a pull-to-open, push-to-close mechanism. A closure bias may be included in the design using a compliant mechanism such as a linear spring, helical spring, or leaf spring. Likewise, other actuation elements can be used for deployment of the gripper elements.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A fixation device for fixation of leaflets of a heart valve comprising:
    an elongate central member defining a longitudinal axis of the fixation device and at least one channel extending along the longitudinal axis;
    first and second arms rotatable about at least one arm hinge point between an open position and a closed position;
    a first gripping element rotatable about a first gripping element axis of rotation to capture a first leaflet of a heart valve between the first gripping element and the first arm;
    a second gripping element rotatable about a second gripping element axis of rotation to capture a second leaflet of a heart valve between the second gripping element and the second arm,
    wherein at least one of the first gripping element axis of rotation and the second gripping element axis of rotation is variably adjustable along the channel of the elongate central member from the arm hinge point by an axis offset distance defined along the longitudinal axis,
    wherein the at least one of the first and second gripping elements is operatively coupled to the at least one channel of the elongate central member and includes a flex portion defining the respective gripping element axis of rotation.

2. The device of claim 1, wherein the at least one channel of the elongate central member is a first and second channel, the first gripping element is operatively coupled to the first channel, and the second gripping element is operatively coupled to the second channel.

3. The device of claim 1, wherein each of the first gripping element axis of rotation and the second gripping element axis of rotation is variably offset from the arm hinge point.

4. The device of claim 3, wherein the axis offset distance includes a first axis offset distance and a second axis offset distance, the first axis offset distance is defined between the arm hinge point and the first gripping element axis of rotation, and the second axis offset distance is defined between the arm hinge point and the second gripping element axis of rotation, wherein the first axis offset distance is independent of the second axis offset distance.

5. The device of claim 1, wherein the first gripping element axis of rotation is parallel to and spaced along the longitudinal axis from the second gripping element axis of rotation.

6. The device of claim 1, wherein the device further including at least one shim disposed in the at least one channel to limit the axis offset distance from a maximum axis offset distance.

7. The device of claim 1, wherein the at least one of the first gripping element axis of rotation and the second gripping element axis of rotation is biased away from the at least one arm hinge point.

8. The device of claim 1, wherein the flex portion includes a first flex portion and a second flex portion, and the first gripping element axis of rotation is comprised of the first flex portion and the second gripping element axis of rotation is comprised of the second flex portion, the first and second flex portions each being defined along a length of the respective gripping element.

9. The device of claim 1, wherein the flex portion is a compliant hinge configured to variably shift the axis offset distance toward or away from the at least one arm hinge point depending on a thickness of a captured native leaflet of the heart valve.

10. The device of claim 1, wherein at least one arm includes a trough having a trough bottom defining a trough reference plane, and further wherein the arm hinge point is offset from the trough reference plane by a trough offset distance defined along the longitudinal axis.

11. The device of claim 1, wherein the fixation device is releasably coupled to a distal end of a delivery shaft.

12. The fixation device of claim 7, further comprising a spring, the spring biasing the at least one of the first gripping element axis of ration and the second gripping element axis of rotation away from the at least one arm hinge point.

13. A fixation device for fixation of leaflets of a heart valve comprising:
an elongate central member defining a longitudinal axis of the fixation device and having a plurality of pin holes defined therein, the plurality of pin holes being spaced apart longitudinally along the elongate central member;
first and second arms rotatable about at least one arm hinge point between an open position and a closed position;
a first gripping element rotatable about a first gripping element axis of rotation to capture a first leaflet of a heart valve between the first gripping element and the first arm;
a second gripping element rotatable about a second gripping element axis of rotation to capture a second leaflet of a heart valve between the second gripping element and the second arm,
wherein at least one of the first gripping element axis of rotation and the second gripping element axis of rotation is defined by a flex portion of the respective gripping element and is variably offset from the arm hinge point by an axis offset distance defined along the longitudinal axis, and
wherein the at least one of the first gripping elements includes at least one connector pin configured to engage with any one of the plurality of pin holes of the elongate central member.

14. The device of claim 12, wherein the first gripping element and the second gripping element are operatively coupled together whereby the first gripping element axis of rotation and the second gripping element axis of rotation define a single axis of rotation.

15. The device of claim 13, wherein the axis offset distance between the at least one hinge point and the at least one of the first gripping element axis of rotation and the second gripping element axis of rotation is incrementally selectable by engaging the at least one connector pin with any one of the plurality of pin holes.

16. A fixation device for fixation of leaflets of a heart valve comprising:
an elongate central member defining a longitudinal axis of the fixation device;
first and second arms rotatable about at least one arm hinge point between an open position and a closed position;
a first gripping element having a first end connected to one of the elongate central member and the first arm, the first gripping element also having a first connection portion connected to the elongate central member and being disposed between the first end and a second end of the first gripping element, the first connection portion having a first flex portion defining a first gripping element axis of rotation such that the first gripping element is rotatable about the first gripping element axis of rotation to capture a first leaflet of a heart valve between the first gripping element and the first arm; and
a second gripping element rotatable about a second gripping element axis of rotation to capture a second leaflet of a heart valve between the second gripping element and the second arm;
wherein the first gripping element axis of rotation is variably offset from the at least one arm hinge point by a first axis offset distance defined along the longitudinal axis; and
wherein the first flex portion is a compliant hinge configured to variably change the first axis offset distance depending on a thickness of a captured native leaflet of the heart valve.

17. The device of claim 16, wherein the first end of the gripping element having the compliant hinge is connected to the elongate central member.

18. The device of claim 16, wherein the first end of the gripping element having the compliant hinge is connected to the corresponding arm.

19. The fixation device of claim 16, wherein the compliant hinge has a zig-zag configuration configured to elongate the first gripping element depending on the thickness of the captured leaflet of the heart valve.

20. The fixation device of claim 16, wherein the second gripping element includes a second connection portion connected to the elongate central member, the second connection portion having a second flex portion defining the second gripping element axis of rotation, the second flex portion being a compliant hinge configured to variable change a second axis offset distance of the second gripping element depending on a thickness of another capture native leaflet of the heart valve.

* * * * *